United States Patent
Bardhan Roy et al.

(10) Patent No.: US 11,738,369 B2
(45) Date of Patent: Aug. 29, 2023

(54) CAPACTIVE MICROMACHINED TRANSDUCER HAVING A HIGH CONTACT RESISTANCE PART

(71) Applicant: GE Precision Healthcare LLC, Milwaukee, WI (US)

(72) Inventors: Rupak Bardhan Roy, Nice (FR); Frederic Lanteri, Le Cannet (FR); Edouard Da Cruz, Nice (FR); Bruno Haider, Rehoboth Beach, DE (US)

(73) Assignee: GE PRECISION HEALTHCARE LLC, Milwaukee, WI (US)

(*) Notice: Subject to any disclaimer, the term of this patent is extended or adjusted under 35 U.S.C. 154(b) by 546 days.

(21) Appl. No.: 16/792,447

(22) Filed: Feb. 17, 2020

(65) Prior Publication Data
US 2021/0252554 A1  Aug. 19, 2021

(51) Int. Cl.
*B06B 1/02* (2006.01)
*A61B 8/00* (2006.01)
*H02N 1/00* (2006.01)

(52) U.S. Cl.
CPC ........... *B06B 1/0292* (2013.01); *H02N 1/006* (2013.01); *A61B 8/4494* (2013.01)

(58) Field of Classification Search
CPC .......... H02N 1/00; H02N 1/002; H02N 1/006; B06B 1/0292; A61B 8/4494; A61B 8/4483
See application file for complete search history.

(56) References Cited

U.S. PATENT DOCUMENTS

| | | | |
|---|---|---|---|
| 7,564,172 B1 | 7/2009 | Huang | |
| 8,618,718 B2 | 12/2013 | Qu et al. | |
| 8,796,901 B2 | 8/2014 | Huang | |
| 10,029,912 B2 | 7/2018 | Huang | |
| 2004/0032185 A1* | 2/2004 | Kato | ...................... H02N 1/006 318/116 |
| 2007/0057603 A1* | 3/2007 | Azuma | ................ H04R 19/005 310/334 |
| 2007/0279457 A1* | 12/2007 | Nystrom | ................. B81B 3/001 347/55 |
| 2010/0207484 A1* | 8/2010 | Chang | ................... B06B 1/0292 310/300 |

(Continued)

FOREIGN PATENT DOCUMENTS

| | | |
|---|---|---|
| EP | 1908529 | 4/2008 |
| EP | 2030698 | 3/2009 |

(Continued)

OTHER PUBLICATIONS

International Application No. PCT/US2021/017199 filed Feb. 9, 2021—International Search Report and Written Opinion dated May 26, 2021; 9 pages.

*Primary Examiner* — Eric Johnson
(74) *Attorney, Agent, or Firm* — McAndrews, Held & Malloy, Ltd.; Jacob Groethe; David Bates

(57) ABSTRACT

A capacitive transducer comprising a top electrode and a bottom electrode, and a sidewall between the top electrode and the bottom electrode. The sidewall is configured to separate the top electrode and the bottom electrode by a gap. There is a high contact resistance part on one or both of a bottom side of the top electrode or a top side of the bottom electrode.

18 Claims, 18 Drawing Sheets

(56) References Cited

U.S. PATENT DOCUMENTS

| | | | |
|---|---|---|---|
| 2012/0018821 A1* | 1/2012 | Beyeler | G01L 1/148 |
| | | | 257/417 |
| 2013/0018269 A1* | 1/2013 | Matsumoto | A61B 8/4494 |
| | | | 600/459 |
| 2013/0135971 A1 | 5/2013 | Nakanishi | |
| 2015/0194560 A1* | 7/2015 | Ayoub | G01T 1/24 |
| | | | 250/371 |
| 2015/0365017 A1 | 12/2015 | Kandori | |
| 2016/0187299 A1 | 6/2016 | Wang et al. | |
| 2017/0326590 A1* | 11/2017 | Daneman | B06B 1/0648 |
| 2019/0366382 A1* | 12/2019 | Akiyama | B06B 1/0215 |

FOREIGN PATENT DOCUMENTS

| | | |
|---|---|---|
| JP | 2016101417 | 6/2016 |
| WO | 2009016606 | 2/2009 |
| WO | 2009139400 | 11/2009 |
| WO | 2010032156 | 3/2010 |
| WO | 2011105602 | 9/2011 |
| WO | 2012020172 | 2/2012 |
| WO | 2012127737 | 9/2012 |
| WO | 2013089648 | 6/2013 |
| WO | 2015135784 | 9/2015 |
| WO | 2018115226 | 6/2018 |
| WO | WO-2021118476 A1 * | 6/2021 |

* cited by examiner

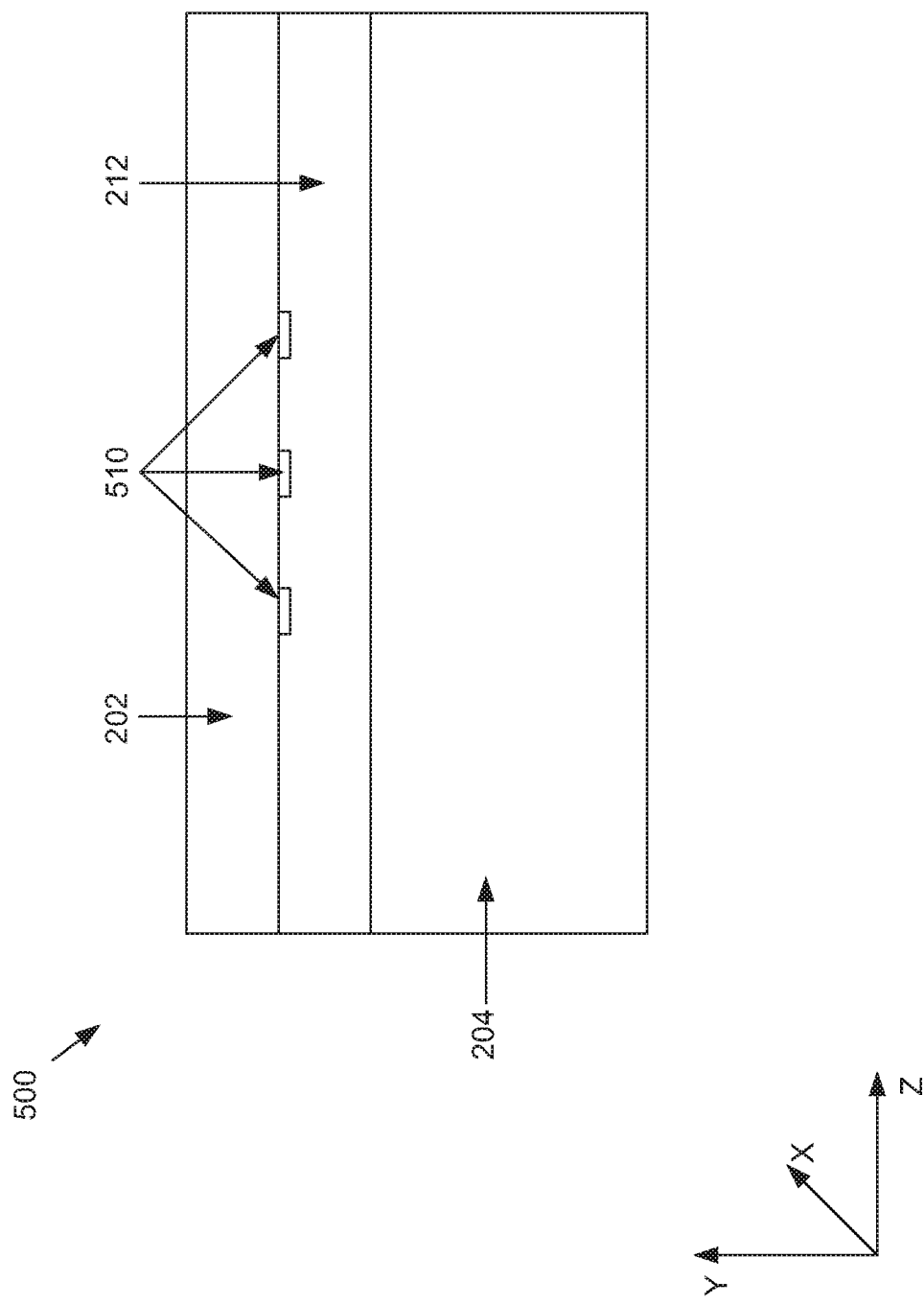

CAPACITIVE MICROMACHINED TRANSDUCER HAVING A HIGH CONTACT RESISTANCE PART

FIELD

Certain embodiments relate to a transducer. More specifically, certain embodiments relate to capacitive micromachined transducer.

BACKGROUND

An ultrasound device may be used for imaging targets such as organs and soft tissues in a human body, as well non-human targets. For example, an ultrasound device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc.

Ultrasound devices may use real time, non-invasive high frequency sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target. A capacitive micromachined ultrasound transducer (CMUT) that is used as a transmit transducer and/or a receive transducer may comprise a top electrode and a bottom electrode, where the top electrode may move due to electrical signals to generate sound waves, or move due to receiving sound waves to generate electrical signals that can be processed. The CMUT may comprise a top electrode that moves and a lower electrode that is stationary, where the top electrode is separated by a gap from the lower electrode. The gap may comprise some level of vacuum or the gap may be filled with, for example, air.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or a method are provided for a capacitive micromachined transducer, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 18 illustrates a view along Z axis of an example capacitive micromachined ultrasound transducer with a high contact resistance bump on a top electrode, in accordance with various embodiments.

DETAILED DESCRIPTION

Figure 1:
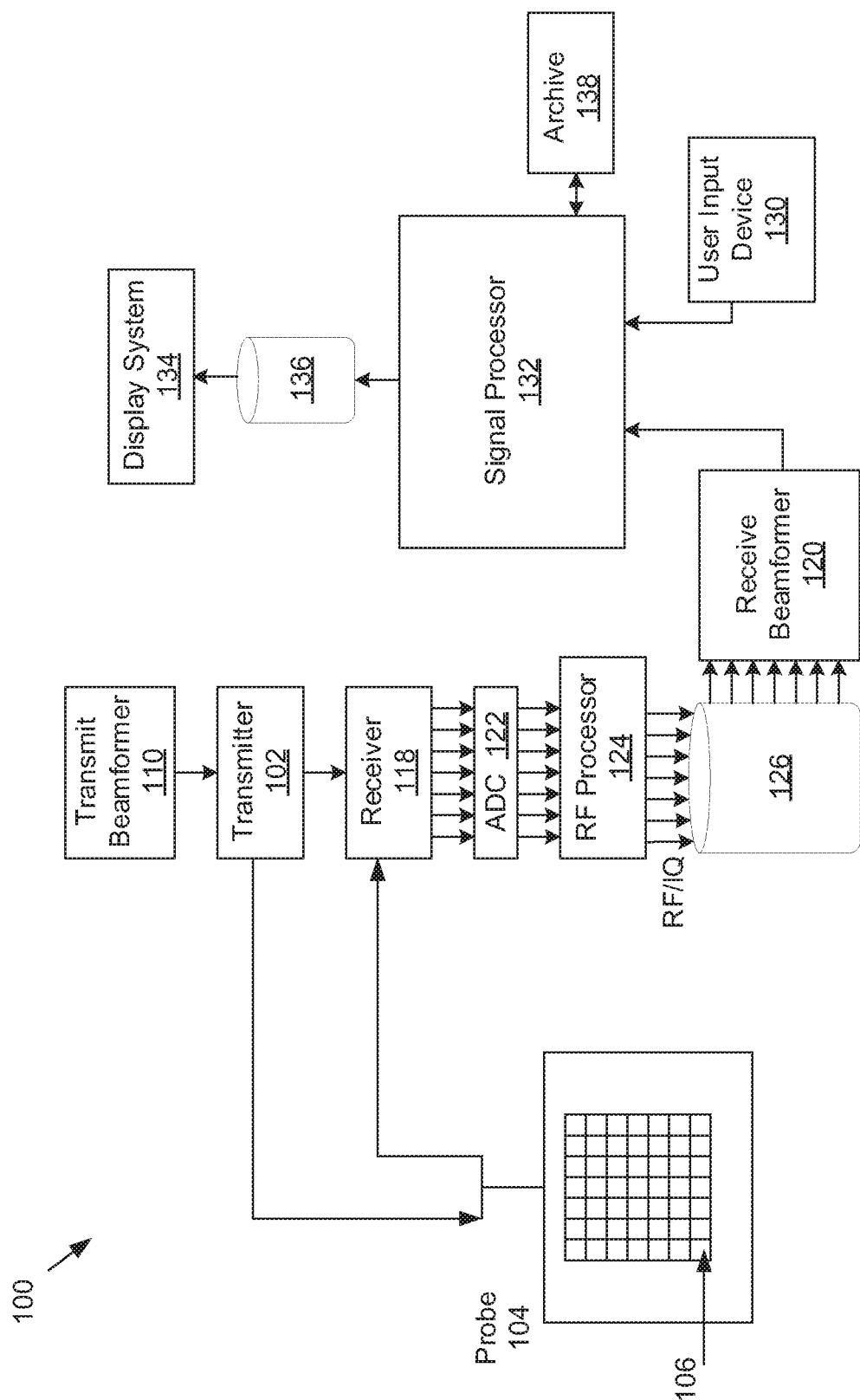
FIG. 1 is a block diagram of an exemplary ultrasound system that may be used in ultrasound imaging, in accordance with various embodiments.

Certain embodiments may be found in a capacitive micromachined transducer. Various embodiments of the disclosure may use a high contact resistance part on a bottom side of the top electrode and/or on a top side of the bottom electrode. This may prevent the top electrode from short circuiting to the bottom electrode when the top electrode is driven too much with electric signals when generating sound waves and/or receiving sound waves to generate corresponding electric signals. Accordingly, this provides for a technical effect of operation by the capacitive micromachined ultrasound transducer (CMUT) without the top electrode short circuiting with the bottom electrode. Additionally, since various embodiments of the present disclosure use high contact resistance material rather than insulating material, a technical effect of alleviating effects of a dielectric charge buildup in CMUT is achieved.

While a CMUT can be used for medical imaging, the CMUT may also be used for various other purposes such as, for example, ultrasound/acoustic sensing, non-destructive evaluation (NDE), ultrasound therapy (e.g., High Intensity Focused Ultrasound (HIFU)), etc., in addition to ultrasound imaging of humans or animals.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. It should be understood that the various embodiments are not limited to the arrangements and instrumentality shown in the drawings. It should also be understood that the embodiments may be combined, or that other embodiments may be utilized and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Additionally, it should be noted that the drawings may not depict objects to scale, but instead strive to present the figures for clarity of explanation.

FIG. 1 is a block diagram of an exemplary ultrasound system that may be used in ultrasound imaging, in accordance with various embodiments. Referring to FIG. 1, there is shown a block diagram of an exemplary ultrasound system 100. The ultrasound system 100 comprises a transmitter 102, an ultrasound probe 104, a transmit beamformer 110, a receiver 118, a receive beamformer 120, A/D converters 122, an RF processor 124, an RF/IQ buffer 126, a user input device 130, a signal processor 132, an image buffer 136, a display system 134, and an archive 138.

The transmitter 102 may comprise suitable logic, circuitry, interfaces and/or code that may be operable to drive the ultrasound probe 104. The ultrasound probe 104 may comprise, for example, a single element CMUT, a 1D array of CMUTs, 2D array of CMUTs, an annular (ring) array of CMUTs, etc. Accordingly, the ultrasound probe 104 may comprise a group of transducer elements 106 that may be, for example, CMUTs. In certain embodiments, the ultrasound probe 104 may be operable to acquire ultrasound image data covering, for example, at least a substantial portion of an anatomy, such as the heart, a blood vessel, or any suitable anatomical structure. Each of the transducer elements 106 may be referred to as a channel.

The transmit beamformer 110 may comprise suitable logic, circuitry, interfaces and/or code that may be operable to control the transmitter 102 that drives the group of transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes can then be received by the transducer elements 106.

The group of transducer elements 106 in the ultrasound probe 104 may be operable to convert the received echoes into analog signals and communicated to a receiver 118. The receiver 118 may comprise suitable logic, circuitry, interfaces and/or code that may be operable to receive the signals from the ultrasound probe 104. The analog signals may be communicated to one or more of the plurality of A/D converters 122.

Accordingly, the ultrasound system 100 may multiplex such that ultrasonic transmit signals are transmitted during certain time periods and echoes of those ultrasonic signals are received during other time periods. Although not shown explicitly, various embodiments of the disclosure may allow simultaneous transmission of ultrasonic signals and reception of echoes from those signals. In such cases, the probe may comprise transmit transducer elements and receive transducer elements.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF data, which may be, for example, I/Q signal data, real valued RF data, etc., may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

Accordingly, various embodiments may have, for example, the RF processor 124 process real valued RF data, or any other equivalent representation of the data, with an appropriate RF buffer 126.

The receive beamformer 120 may comprise suitable logic, circuitry, interfaces and/or code that may be operable to perform digital beamforming processing to sum, for example, delayed, phase shifted, and/or weighted channel signals received from the RF processor 124 via the RF/IQ buffer 126 and output a beam summed signal. The delayed, phase shifted, and/or weighted channel data may be summed to form a scan line output from the receive beamformer 120, where the scan line may be, for example, complex valued or non-complex valued. The specific delay for a channel may be provided, for example, by the RF processor 124 or any other processor configured to perform the task. The delayed, phase shifted, and/or weighted channel data may be referred to as delay aligned channel data.

The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 may comprise a plurality of receive beamformers 120.

The user input device 130 may be utilized to input patient data, scan parameters, settings, select protocols and/or templates, and the like. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include switch(es), button(s), rotary encoder(s), a touchscreen, motion tracking, voice recognition, a mouse device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may comprise a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in a live or off-line operation. In various embodiments, the processed image data can be presented at the display system 134 and/or stored at the archive 138. The archive 138 may be a local archive, a Picture Archiving and Communication System (PACS), or any suitable device for storing images and related information.

The signal processor 132 may comprise one or more central processing units, microprocessors, microcontrollers, and/or the like. The signal processor 132 may be an integrated component, or may be distributed across various locations, for example. In an exemplary embodiment, the signal processor 132 may be capable of receiving input information from the user input device 130 and/or the archive 138, generating an output displayable by the display system 134, and manipulating the output in response to input information from the user input device 130, among other things. The signal processor 132 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates may range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes worth of frames of ultrasound scan data. The frames of ultrasound scan data are stored in a manner to facilitate retrieval thereof according to its order or time of acquisition. The image buffer 136 may be embodied as any known data storage medium.

The display system 134 may be any device capable of communicating visual information to a user. For example, a display system 134 may include a liquid crystal display, a light emitting diode display, and/or any suitable display or displays. The display system 134 can be operable to present ultrasound images and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display. Additionally, while the ultrasound system 100 was described to comprise a receive beamformer 120, an RF processor 124, and a signal processor 132, various embodiments of the disclosure may use various number of processors. For example, various devices that execute code may be referred to generally as processors. Various embodiments may refer to each of these devices, including each of the RF processor 124 and the signal processor 132, as a processor. Furthermore, there may be other processors to additionally perform the tasks described as being performed by these devices, including the receive beamformer 120, the RF processor 124, and the signal processor 132, and all of these processors may be referred to as a "processor" for ease of description.

Certain applications may find it desirable to drive CMUTs hard enough so that they operate in collapse mode. That is, the top electrode is driven to the bottom electrode. This may permit the CMUTs to provide higher levels of acoustic power, more linearity and wider bandwidth during operation. However, this may result in the top electrode contacting the bottom electrode, resulting in an electrical short circuit of the electrodes that may cause permanent damage to the structure of the CMUT. To avoid this problem, one or more insulation layers or bumps are sandwiched between the bottom and top electrode. An electrical reliability issue generally originates substantially from charging problem caused by trapped charges in the thin dielectric insulation layers. While various efforts have been made to overcome this problem, industrial CMUT devices to date have not been able to overcome the problems associated with operating in collapse mode due to reliability issues. Two most important causes for the trapped charges are the fabrication process CMUT, and strong electrical field in the gap during operation of the CMUT.

Charges can be trapped either on the surface or within a dielectric insulation layer that may be present in a convention CMUT. The trapped charges shield the electrode surface with unintended effects depending on the amplitude and frequency of the drive signal superimposed on the DC bias. Additionally, such charges can cause issues during membrane snapback after collapse.

While some solutions offered both from academics and industry include the use of PostCMUTs, spacers (membrane bumps), extended edge insulator thickness, etc., these approaches merely localized the charging issue to smaller regions. The charge trapping still occurs, and, therefore, the problem still exists.

Various embodiments of the disclosure provide for a high contact resistance material isolating the top and bottom electrodes. For a two electrode system, specific contact resistivity ($R_c$) is experimentally defined as the slope of the I-V curve at V=0 and is mathematically defined as:

$$R_c = \left\{ \frac{\partial V}{\partial J} \right\}_{v=0} \quad \text{(Equation 1)}$$

where J is the current density. The units of specific contact resistivity is $\Omega*cm^2$. When the current is a linear function of the voltage, the device is said to have ohmic contacts. Contact resistance can be different from the volume resistivity of a material.

Materials with higher ohmic contact resistance come from, for example, semi-insulating III-V or II-VI materials of the periodic table like Gallium Arsenide (GaAs), Cadmium Zinc Telluride (CdZnTe), etc. In semiconductor industry such materials may be used extensively in transistor and sensors but only with metal deposition to bring the contact resistance down substantially. The electrical contact resistivity of such material may be, for example, greater than $10^7$ $\Omega*cm^2$. The contact resistance phenomenon is primarily exhibited by the high transient resistances of the electrodes or near contact regions of the electrodes. The contact resistance of such materials may be comparable or in some cases much higher than the bulk resistance. Thin layers of such materials may be deposited, for example, using atomic layer deposition process.

Therefore, it can be seen that with respect to collapsed electrodes, a layer or contact spacer(s) of such high contact resistance material can be used without the problems caused by trapped charges in dielectrics. Additionally, the DC bias requirement is benchmarked with respect to the collapsed voltage. The DC bias voltage is predominantly related to the effective gap height between the top electrode and the bottom electrode. The effective gap height for using a dielectric is the sum of the static gap and a thickness of the dielectric scaled by the dielectric constant of the insulation layer material. Similarly, the effective gap height for using a high contact resistance material is the sum of the static gap and a thickness of the high contact resistance material scaled by the dielectric constant of the high contact resistance material.

The equation for collapsed voltage $V_{col}$ is shown below in Equations 2 and 3:

$$V_{col} = \sqrt{\frac{8K g_{eff}^3}{27\varepsilon_0 A}} \quad \text{(Equation 2)}$$

where, K is membrane stiffness, $\varepsilon_0$ is permittivity of free space, and A is the device area. The effective gap height is given by:

$$g_{eff} = g_0 + \frac{t_r}{\varepsilon_r} \quad \text{(Equation 3)}$$

where $g_0$ is the vacuum/air gap, is the high contact resistance layer thickness, and $\varepsilon_v$ is the permittivity of the insulation material.

Accordingly, it can be seen that CMUTs that use high contact resistance material that is thinner than insulating dielectric material can reduce the DC requirement of a specific CMUT configuration and hence increase both transmit and receive sensitivity. Additionally, using the high contact resistance material removes dielectric charging effects and other functional complexities, hence increasing device reliability.

It should be noted that while high contact resistance material can come from III-V or II-VI materials of the periodic table, various embodiments of the disclosure may use other materials that offer suitable high contact resistance characteristics.

FIGS. 2-17 illustrate cross-sections of various configurations for capacitive micromachined ultrasound transducers that may be used with high contact resistance materials. While some configurations are shown, it should be understood that the disclosure allows for various other configurations that may also be used for CMUTs.

Figure 2:
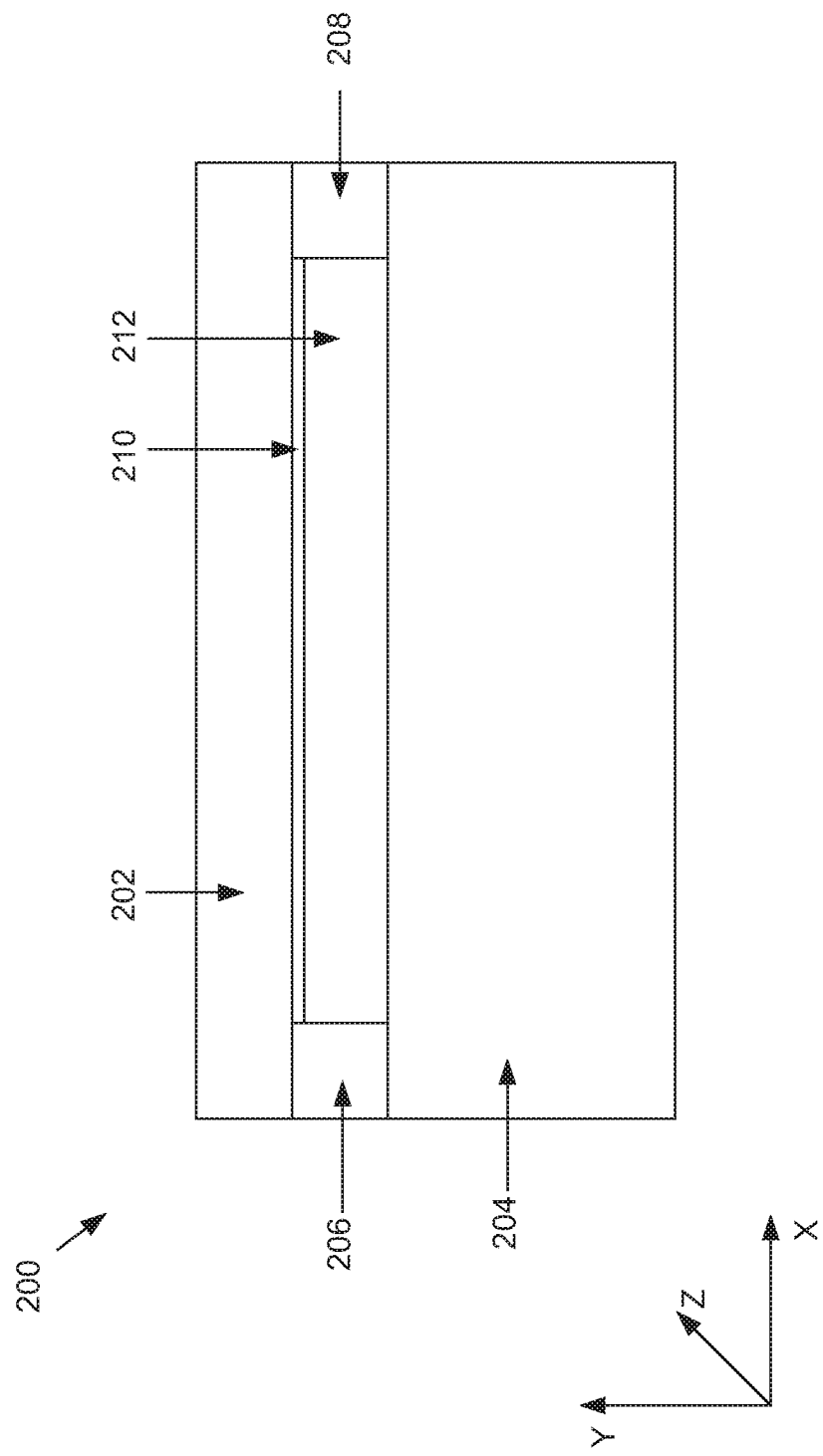
FIG. 2 illustrates an example capacitive micromachined ultrasound transducer with a high contact resistance layer on a top electrode, in accordance with various embodiments.
Figure 3:
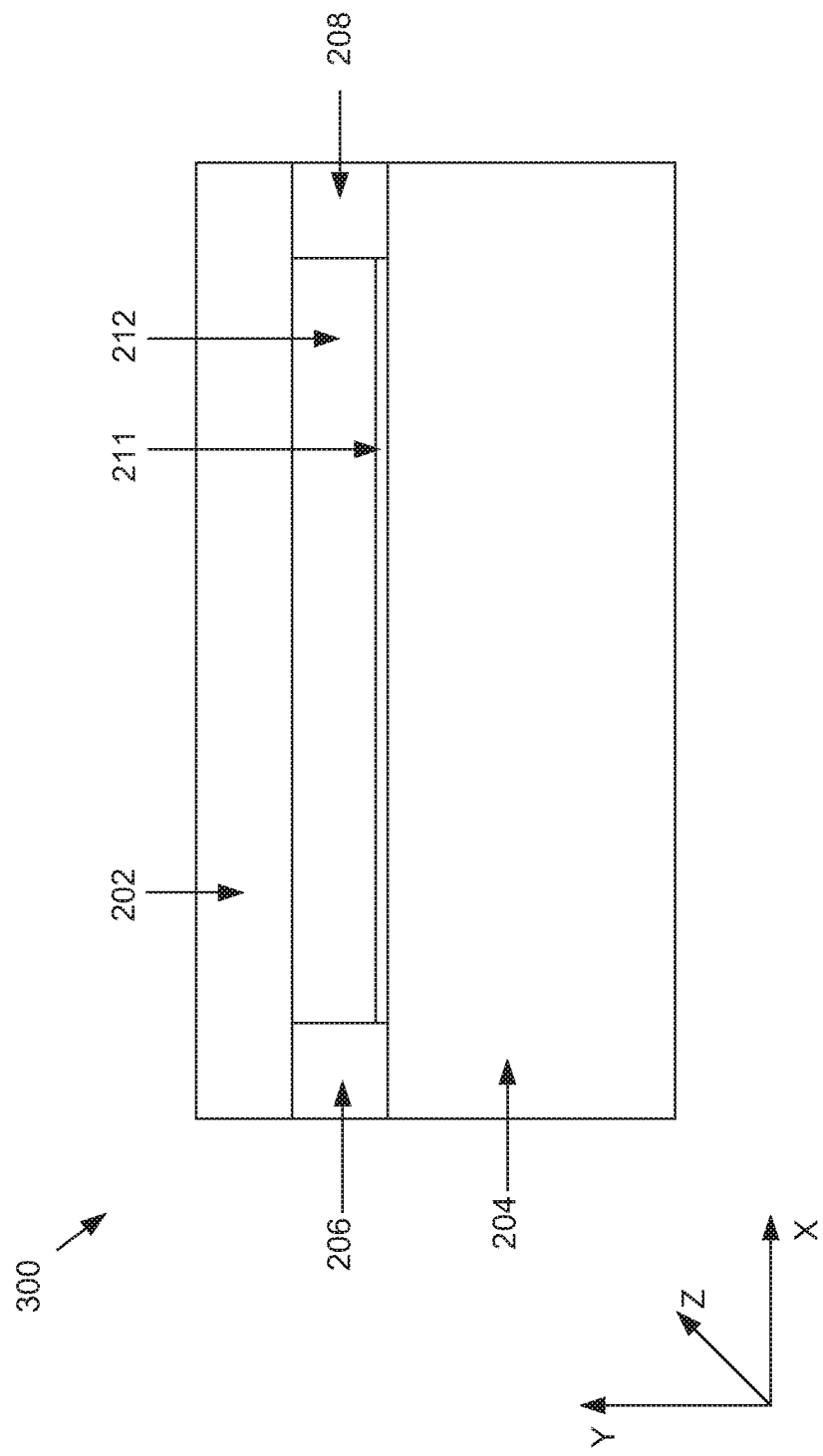
FIG. 3 illustrates an example capacitive micromachined ultrasound transducer with a high contact resistance layer on a bottom electrode, in accordance with various embodiments.
Figure 4:
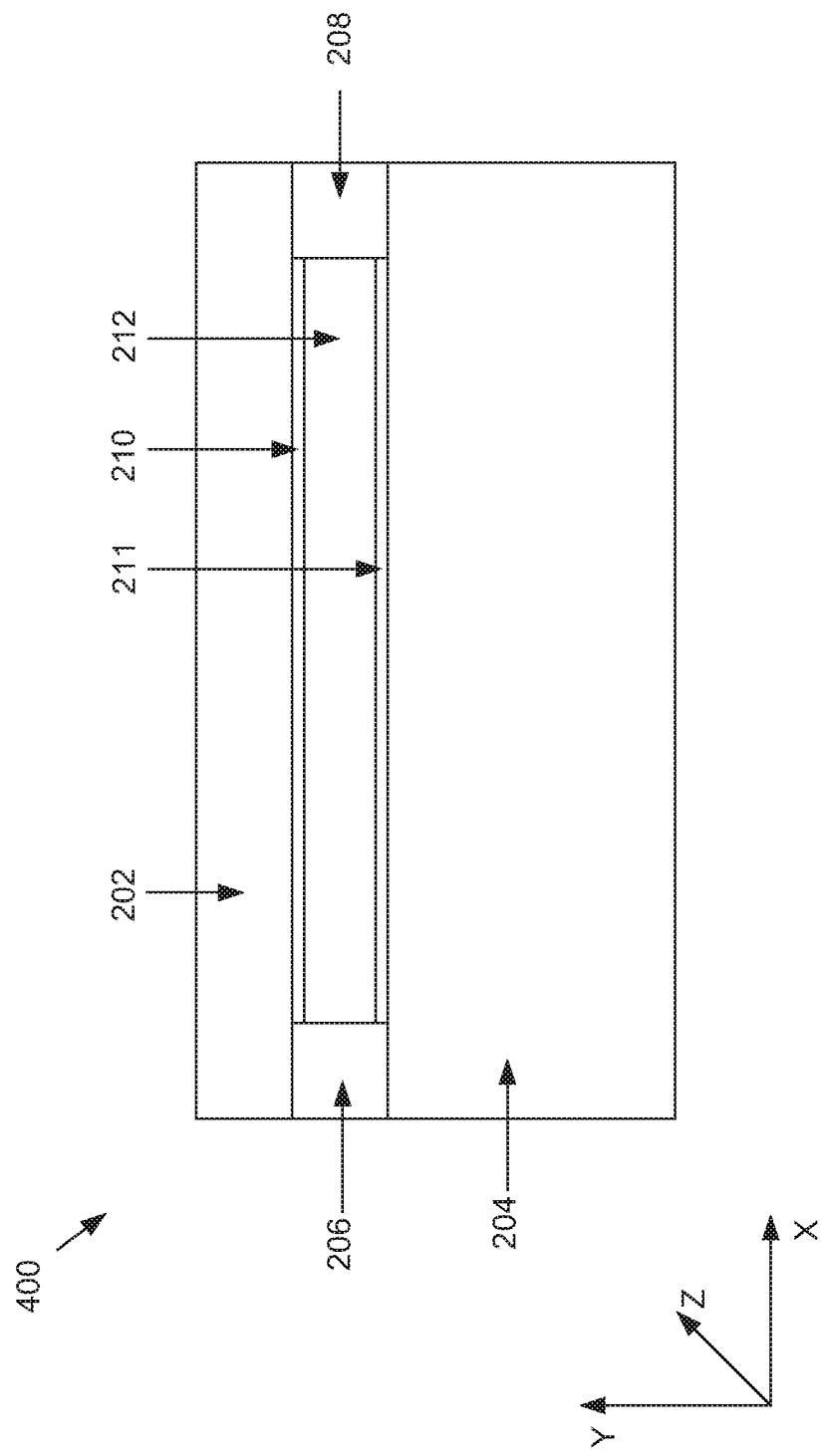
FIG. 4 illustrates an example capacitive micromachined ultrasound transducer with a high contact resistance layer on both the top electrode and the bottom electrode, in accordance with various embodiments.

FIGS. 2-4 illustrate various examples of capacitive micromachined ultrasound transducers using a high contact resistance layer on the top electrode and/or the bottom electrode. For example, FIG. 2 comprises a cross-section view of a CMUT 200 with a top electrode 202, a bottom electrode 204, sidewalls 206 and 208, the top layer 210 made of high contact resistance material, and a gap 212 that may be filled with gas, such as, for example, air, or may comprise some level of vacuum. Accordingly, the sidewalls 206/208 may define the effective gap ($g_{eff}$) comprising the top high contact resistance layer 210 and the gap 212.

Generally, while various figures, including FIG. 2, show what appears to be separate sidewalls 206/208 in the cross-section views, it should be understood that the sidewalls 206/208 may be parts of a continuous sidewall or may be separate sidewalls.

FIG. 3 is similar to FIG. 2, except that there is a bottom layer 211 made of high contact resistance material rather than the top layer 210. Accordingly, the sidewalls 206/208 may define the effective gap ($g_{eff}$) comprising the bottom layer 211 and the gap 212.

While FIGS. 2 and 3, as well as other figures, show the top layer 210 and the bottom layer 211 as extending from the sidewall 206 to the sidewall 208, various embodiments of the disclosure may have the top layer 210 and/or the bottom layer 211 extending under the sidewalls 206 and/or 208.

While FIGS. 2 and 3, as well as other figures, show the top layer 210 and the bottom layer 211 as extending from the sidewall 206 to the sidewall 208, the top layer 202 and/or the bottom layer 204 may extend only a portion of the width between the sidewalls 206 and 208.

FIG. 4 combines FIGS. 2 and 3 so that there is the top layer 210 and the bottom layer 211. Accordingly, the sidewalls 206/208 may define the effective gap ($g_{eff}$) comprising the top and bottom layers 210/211 and the gap 212.

The top layer 210 and/or the bottom layer 211 may extend substantially over an area in the X-Z plane for the CMUT, or for a partial area in the X-Z plane. When the layer 210/211 forms a partial area in the X-Z plane, it may be referred to as a bump. A bump may be different sizes in terms of area. FIGS. 5-18 show bumps that are a fraction of a length of a CMUT. However, various embodiments of the disclosure need not be limited so.

Figure 5:
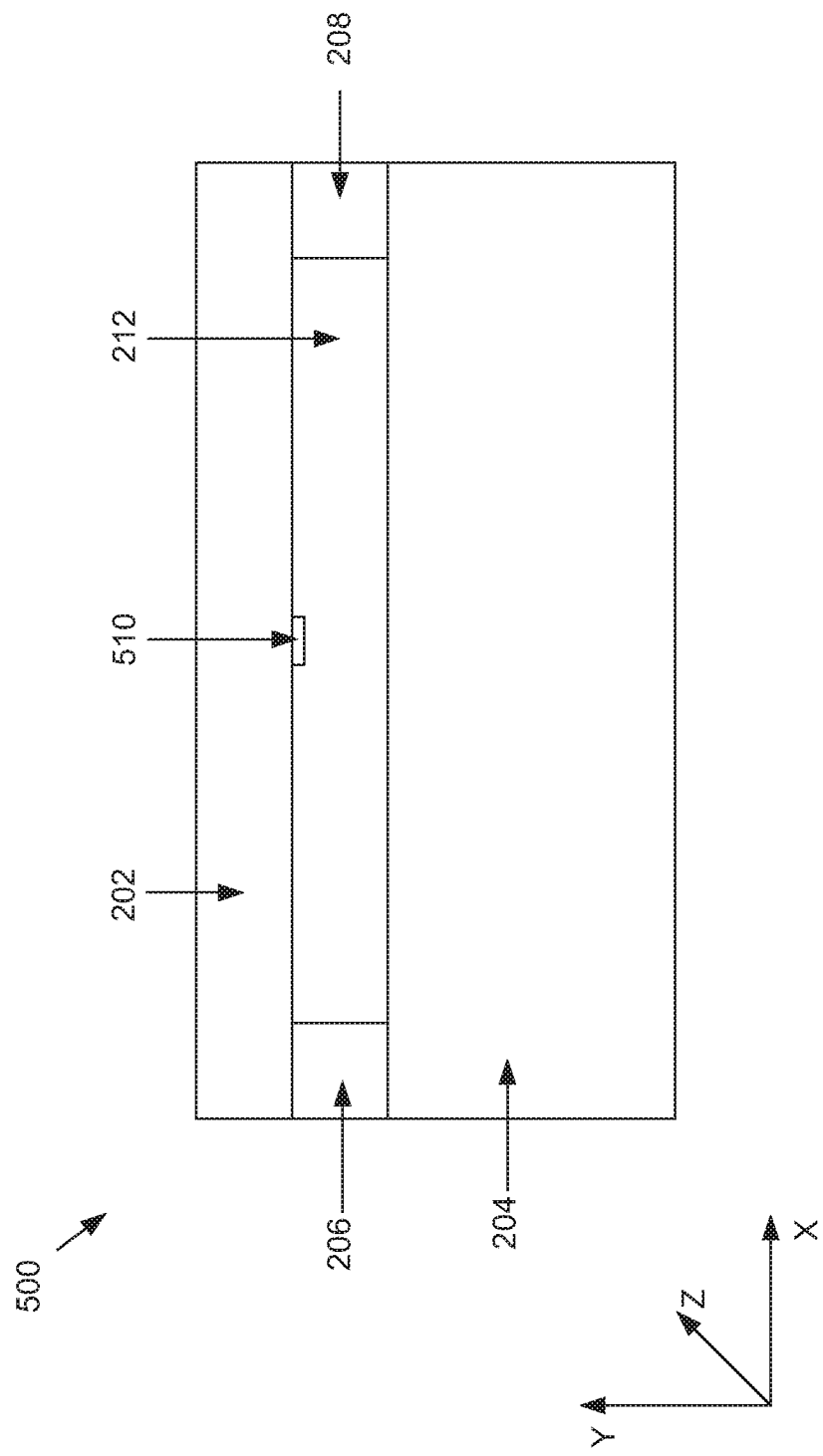
FIG. 5 illustrates an example capacitive micromachined ultrasound transducer with a rectangular high contact resistance bump on a top electrode, in accordance with various embodiments.
Figure 6:
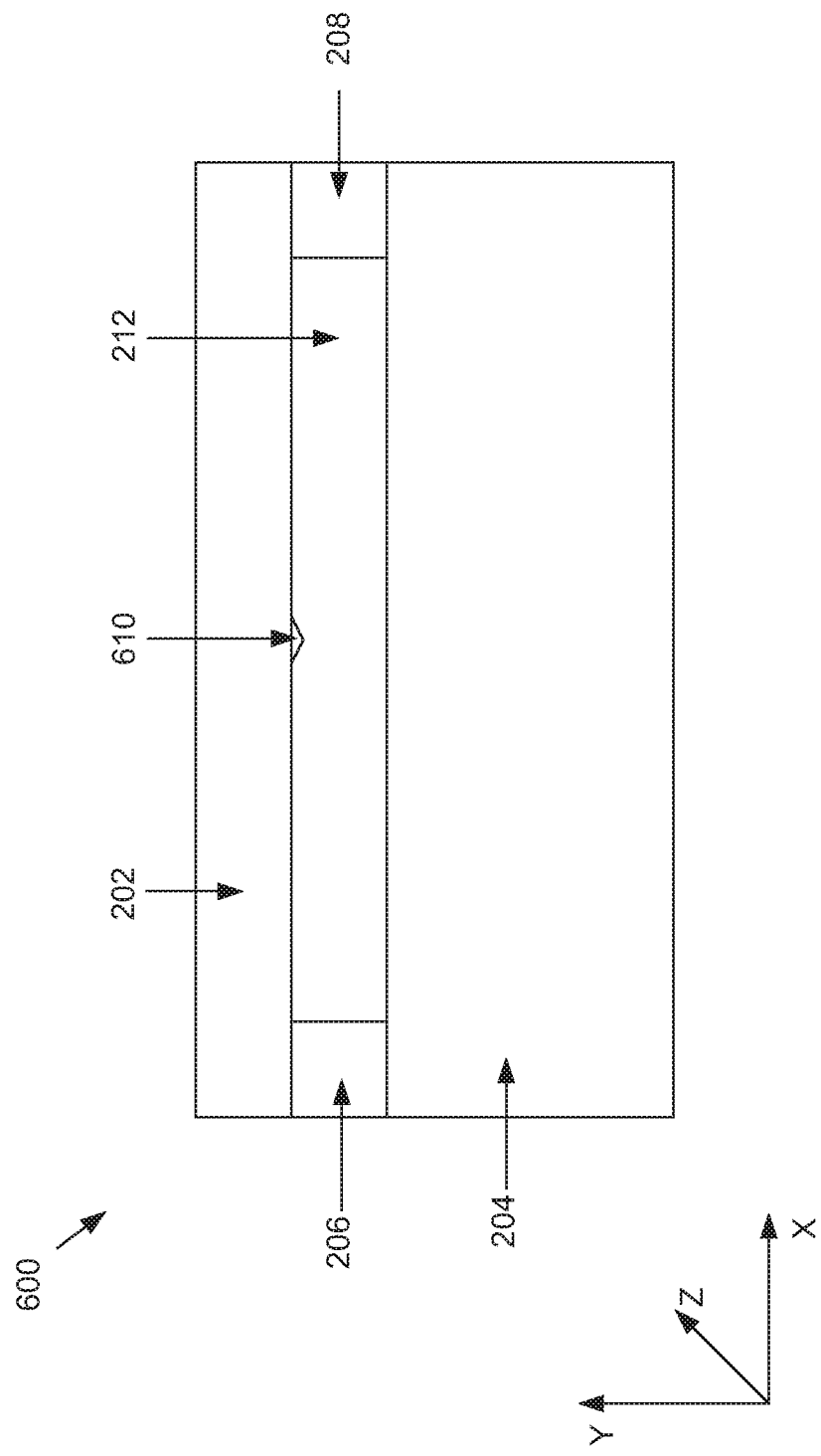
FIG. 6 illustrates an example capacitive micromachined ultrasound transducer with a triangular high contact resistance bump on a top electrode, in accordance with various embodiments.
Figure 7:
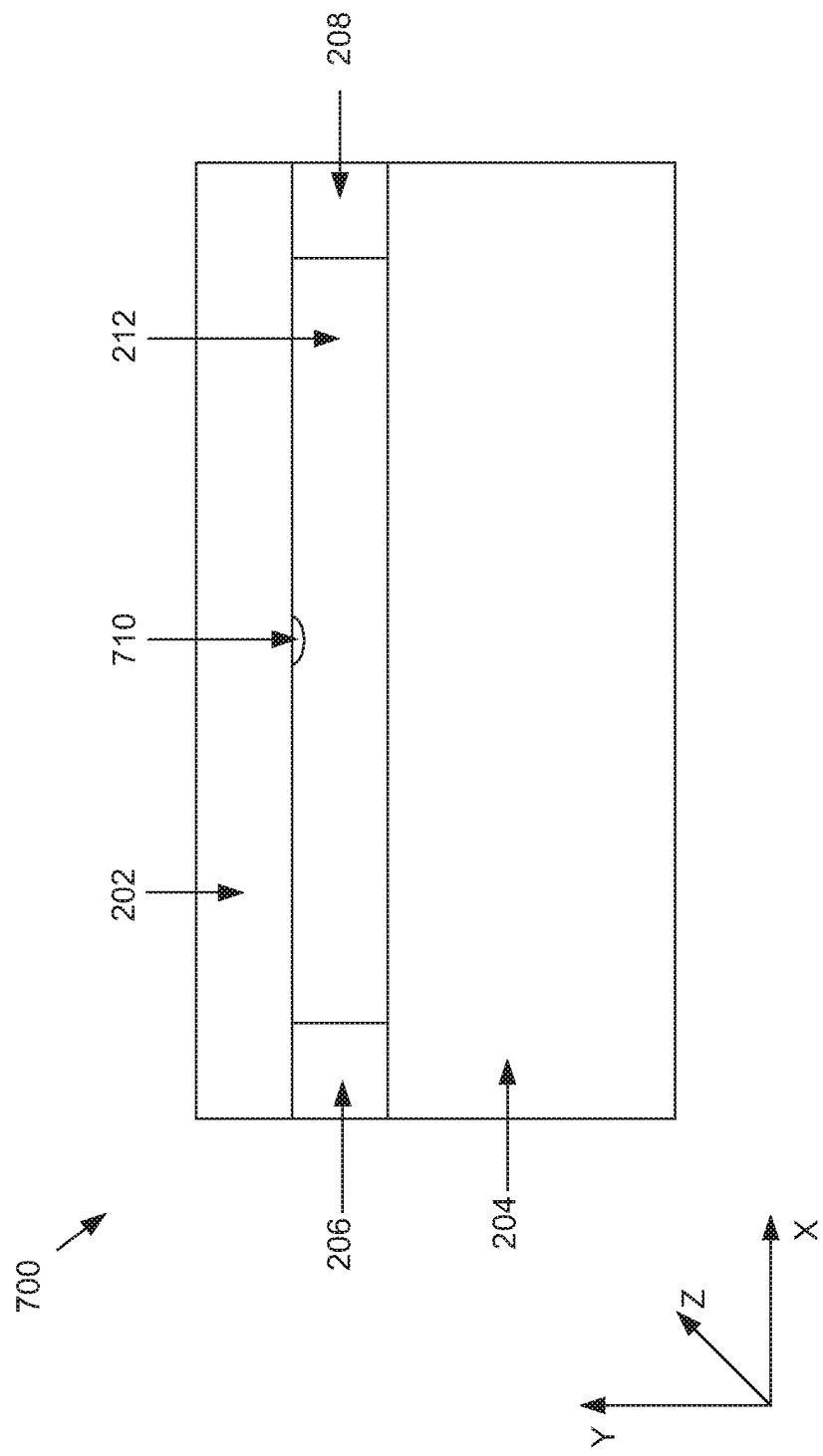
FIG. 7 illustrates an example capacitive micromachined ultrasound transducer with a rounded high contact resistance bump on a top electrode, in accordance with various embodiments.

FIGS. 5-7 illustrate various examples of capacitive micromachined ultrasound transducers using a bump made of high contact resistance material. Each of the bumps 510, 610, 710 may be substantially centered, for example, across a width of the top electrode 202 (e.g., along a direction X of the CMUT). However, various embodiments of the disclosure may put the bump at a different location that is not centered. A bump may be various shapes such as, for example, the rectangular bump 510, a triangular bump 610, and a rounded bump 710. Accordingly, the sidewalls 206/208 may define the effective gap ($g_{eff}$) comprising the bump 510, 610, or 710 and the gap 212.

Additionally, as the FIGS. 5-7 show respective cross-section views of the CMUT 500-700, each bump may extend into the Z direction of a CMUT (into and out of the paper) or there may be multiple bumps in the Z direction. Additionally, as a cross-section of a bump is shown, a bump may comprise any shape where a cross-section of the bump is rectangular, triangular, rounded, etc. Where there is a single bump in the X direction, as shown, for example, in FIGS. 5-7, the bump may be substantially centered along the X axis of the CMUT. However, various embodiments may place the bump so that it is not substantially centered along the X axis of the CMUT.

Figure 8:
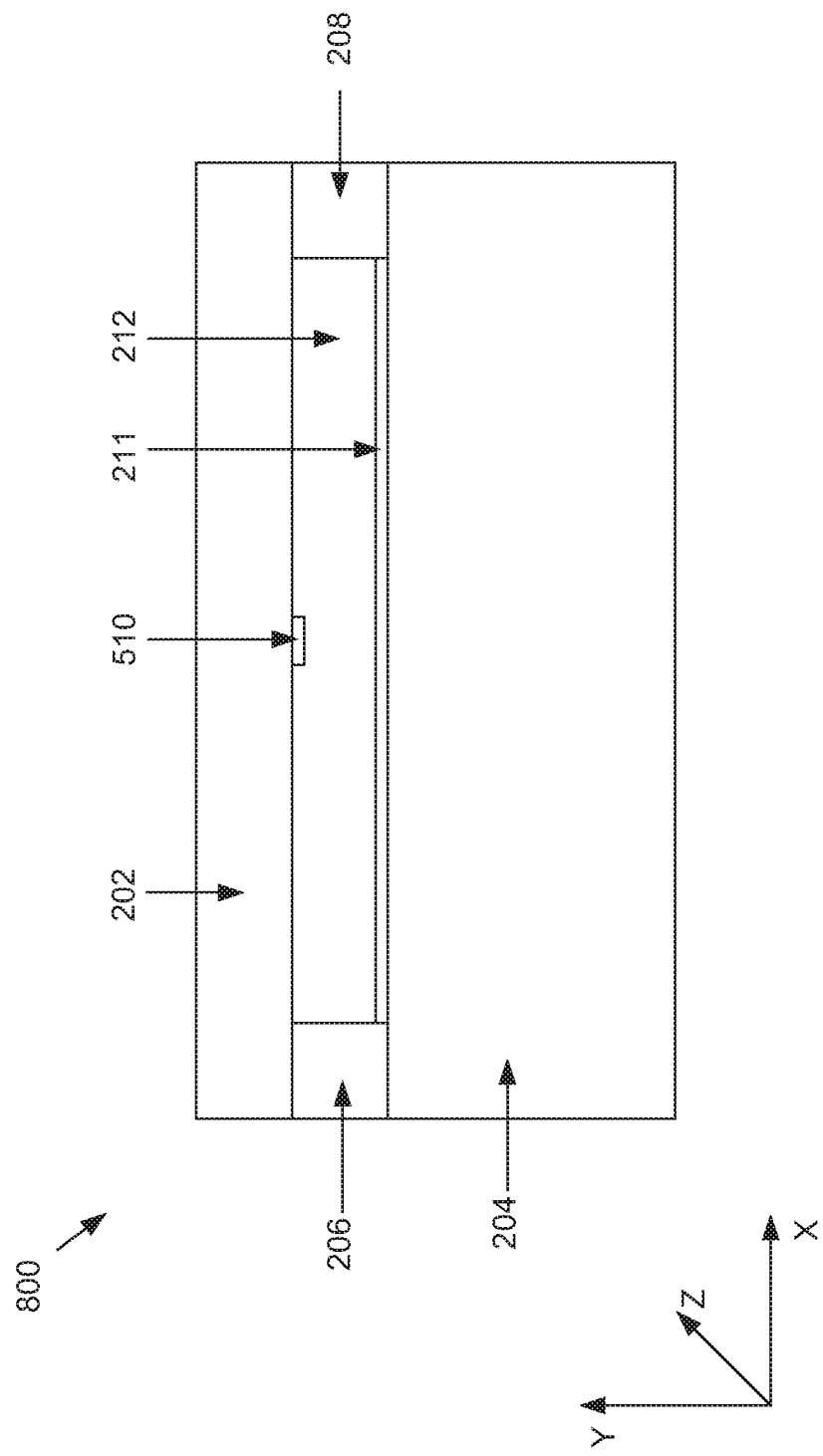
FIG. 8 illustrates an example capacitive micromachined ultrasound transducer with a rectangular high contact resistance bump on a top electrode and a high contact resistance layer on a bottom electrode, in accordance with various embodiments.
Figure 9:
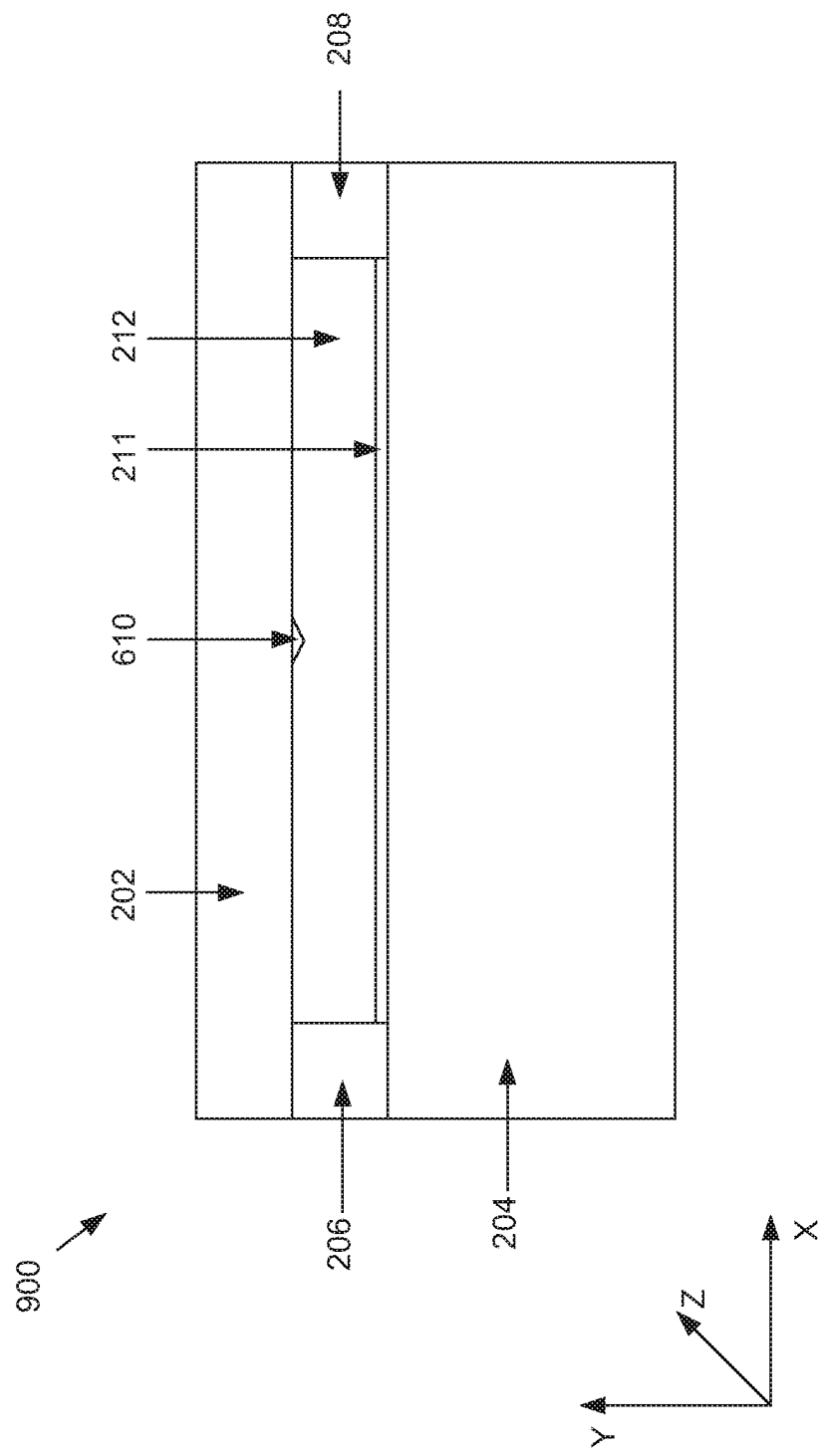
FIG. 9 illustrates an example capacitive micromachined ultrasound transducer with a triangular high contact resistance bump on a top electrode and a high contact resistance layer on a bottom electrode, in accordance with various embodiments.
Figure 10:
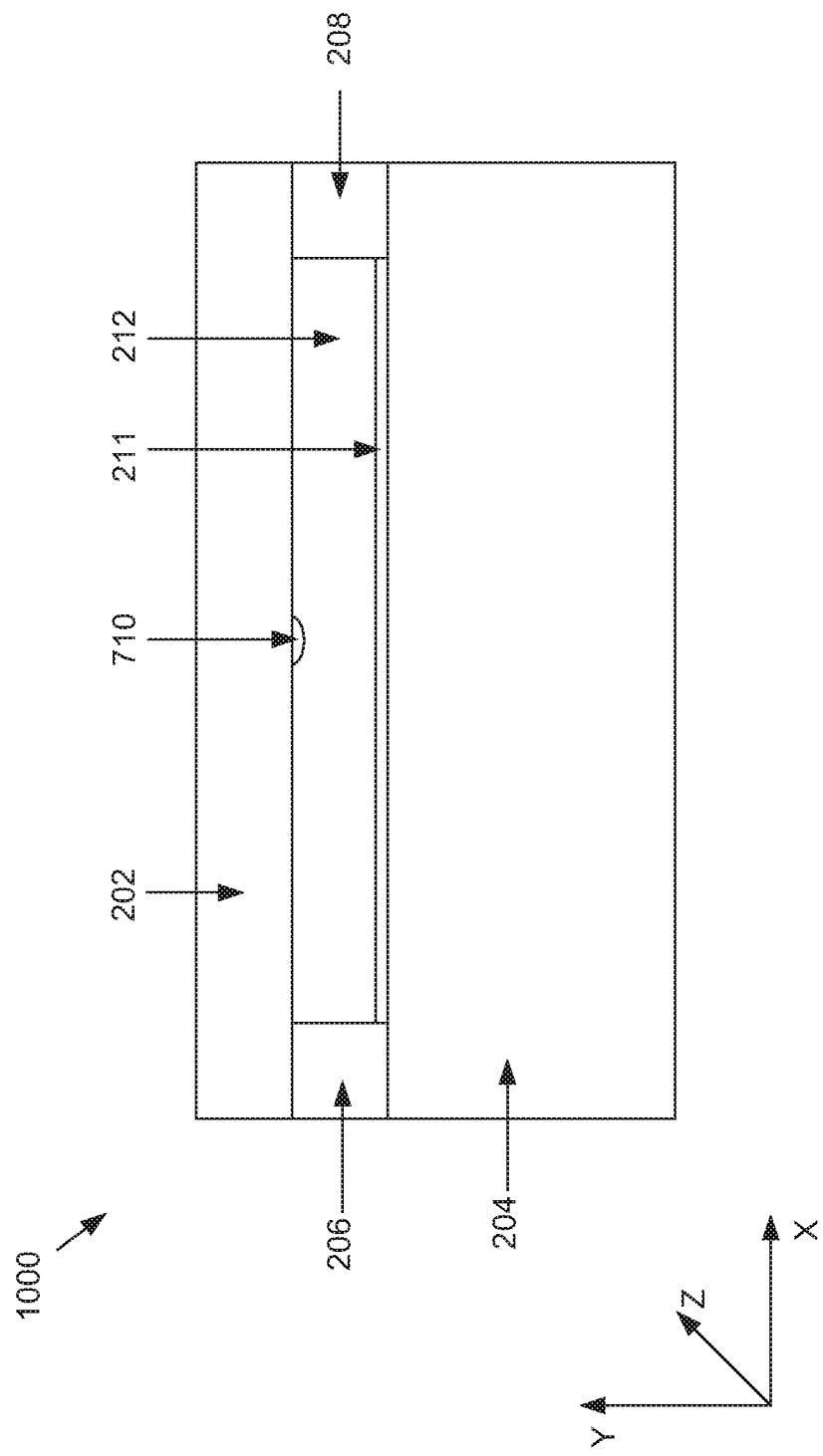
FIG. 10 illustrates an example capacitive micromachined ultrasound transducer with a rounded high contact resistance bump on a top electrode and a high contact resistance layer on a bottom electrode, in accordance with various embodiments.

FIGS. 8-10 illustrate various examples of capacitive micromachined ultrasound transducers with a bump 510, 610, or 710 on the top electrode 202 and a high contact resistance layer 211 on the bottom electrode 204. For example, FIG. 8 shows a cross-section view of a CMUT 800 comprising a rectangular bump 510 and a bottom layer 211. FIG. 9 shows a cross-section view of a CMUT 900 comprising a triangular bump 610 and a bottom layer 211. FIG. 10 shows a cross-section view of a CMUT 1000 comprising a rounded bump 710 and a bottom layer 211. Accordingly, the sidewalls 206/208 may define the effective gap ($g_{eff}$) comprising the bump 510, 610, or 710, the bottom high contact resistance layer 211, and the gap 212.

Figure 11:
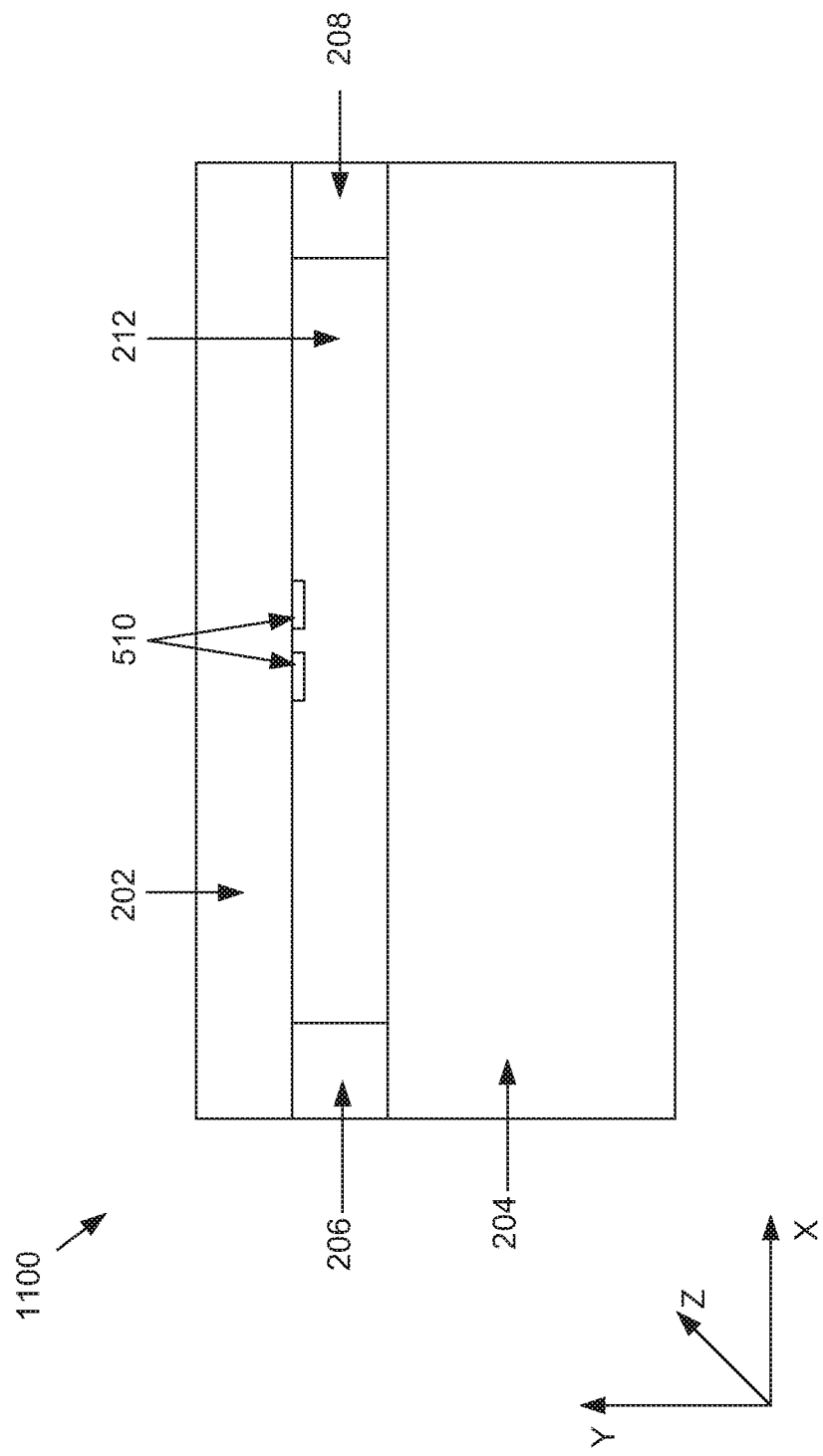
FIG. 11 illustrates an example capacitive micromachined ultrasound transducer with multiple high contact resistance bumps on a top electrode, in accordance with various embodiments.
Figure 12:
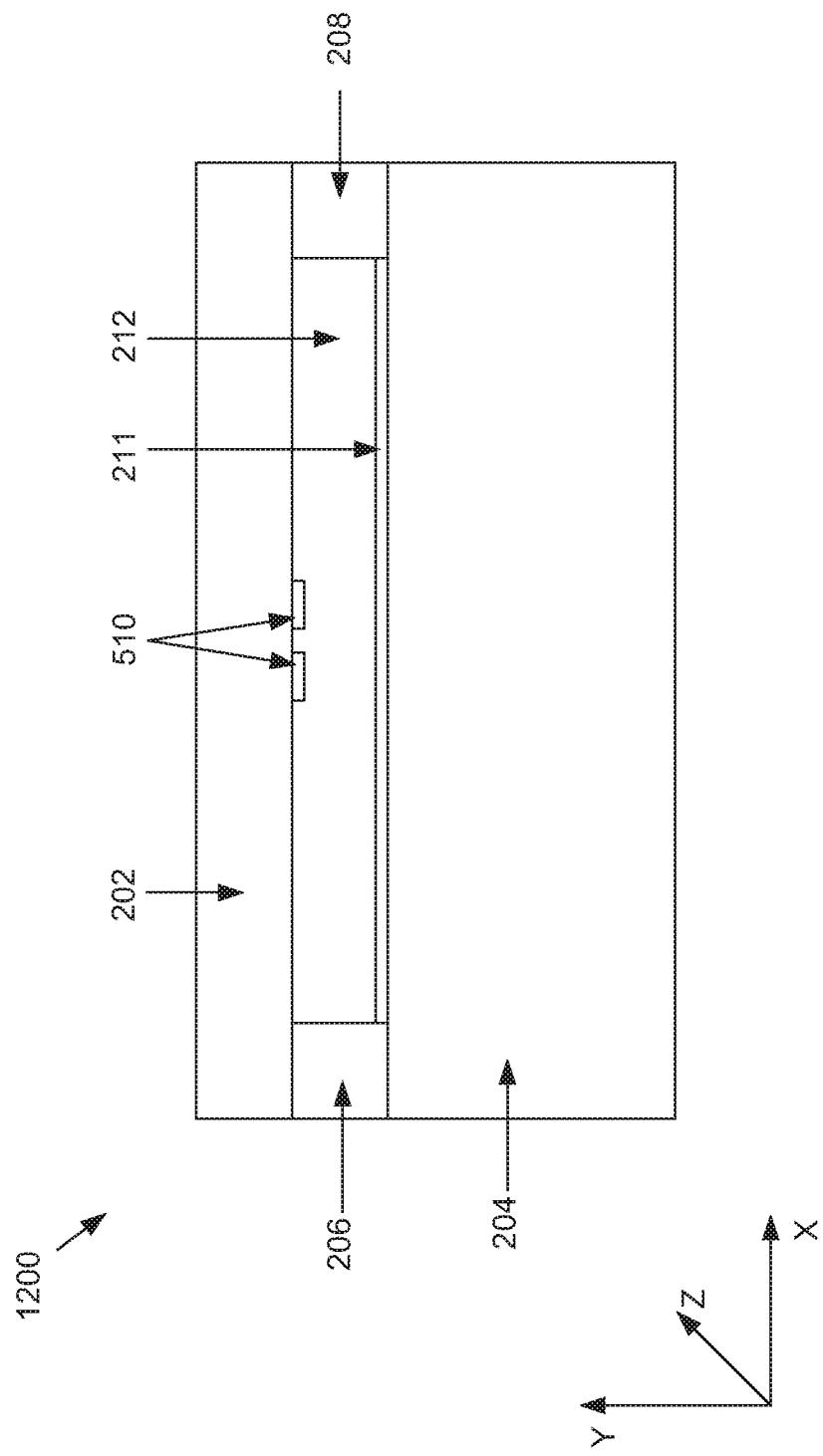
FIG. 12 illustrates an example capacitive micromachined ultrasound transducer with multiple high contact resistance bumps on a top electrode and a high contact resistance layer on a bottom electrode, in accordance with various embodiments.

FIGS. 11-12 illustrate examples of capacitive micromachined ultrasound transducer (CMUT) with multiple high contact resistance bumps 510 on a top electrode 202. While two bumps 510 are shown, there may be more than two bumps 510. Additionally, while the bumps 510 are shown to be substantially centered across a width of the top electrode 202 (e.g., along the direction X), various embodiments of the disclosure may place the bumps 510 at different positions. FIG. 11 illustrates a configuration similar to that shown for CMUT 500 in FIG. 5 except that there are two bumps 510. Accordingly, the sidewalls 206/208 may define the effective gap ($g_{eff}$) comprising the bump 510 and the gap 212.

FIG. 12 illustrates a configuration similar to that shown for CMUT 800 in FIG. 8 except that there are two bumps 510. Accordingly, the sidewalls 206/208 may define the effective gap ($g_{eff}$) comprising the bump 510, the bottom high contact resistance layer 211, and the gap 212.

Where there are multiple bumps in the X direction, as shown, for example, in FIGS. 11-12, 14, and 17-18, the bumps as a unit may be substantially centered along the X axis of the CMUT. However, various embodiments may place the bumps so that they are not substantially centered as a unit along the X axis of the CMUT. Accordingly, any of the individual bumps may be placed in different positions along a dimension of the CMUT.

Figure 13:
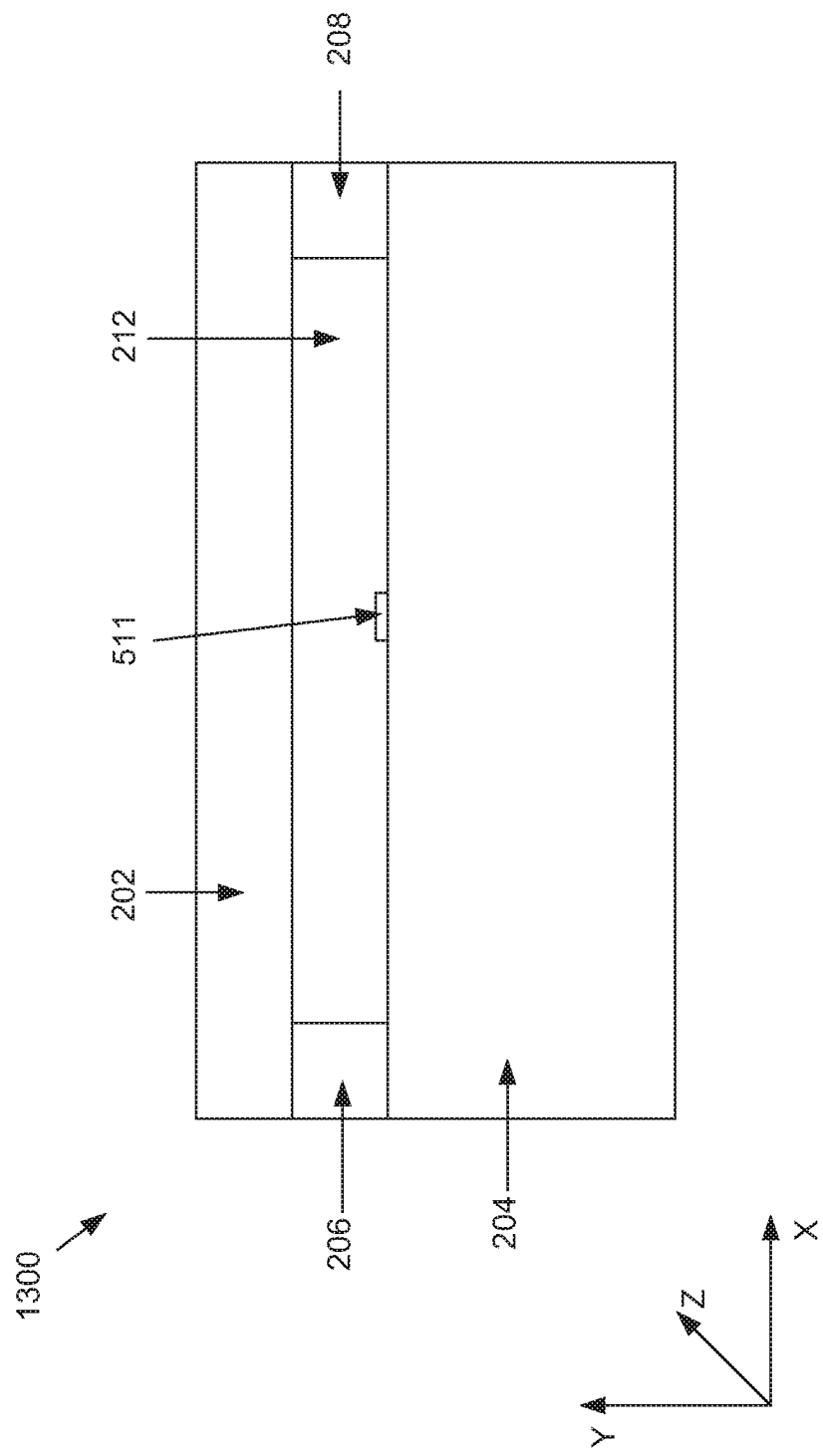
FIG. 13 illustrates an example capacitive micromachined ultrasound transducer with a high contact resistance bump on a bottom electrode, in accordance with various embodiments.

FIG. 13 illustrates an example capacitive micromachined ultrasound transducer similar to the CMUT 500 of FIG. 5 except that a high contact resistance bump 511 on the bottom electrode 204 is shown rather than high contact resistance bump 510 on the bottom electrode 202. Accordingly, the sidewalls 206/208 may define the effective gap ($g_{eff}$) comprising the bump 511 and the gap 212.

Figure 14:
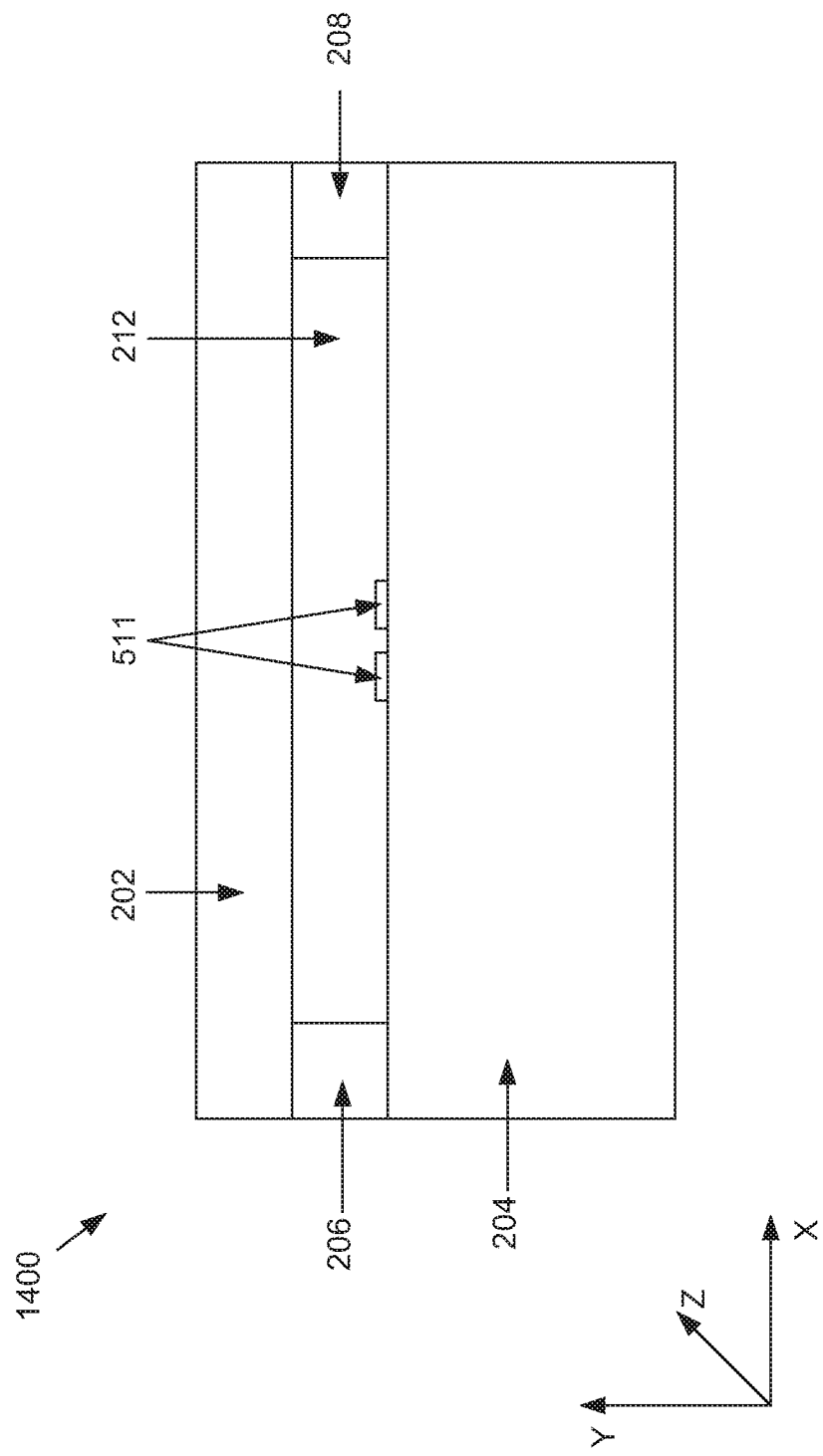
FIG. 14 illustrates an example capacitive micromachined ultrasound transducer with multiple high contact resistance bumps on a bottom electrode, in accordance with various embodiments.

FIG. 14 illustrates an example capacitive micromachined ultrasound transducer similar to the CMUT 1100 of FIG. 11 except that high contact resistance bumps 511 on the bottom electrode 204 are shown rather than high contact resistance bumps 510 on the bottom electrode 202. Accordingly, the sidewalls 206/208 may define the effective gap ($g_{eff}$) comprising the bumps 511 and the gap 212.

Figure 15:
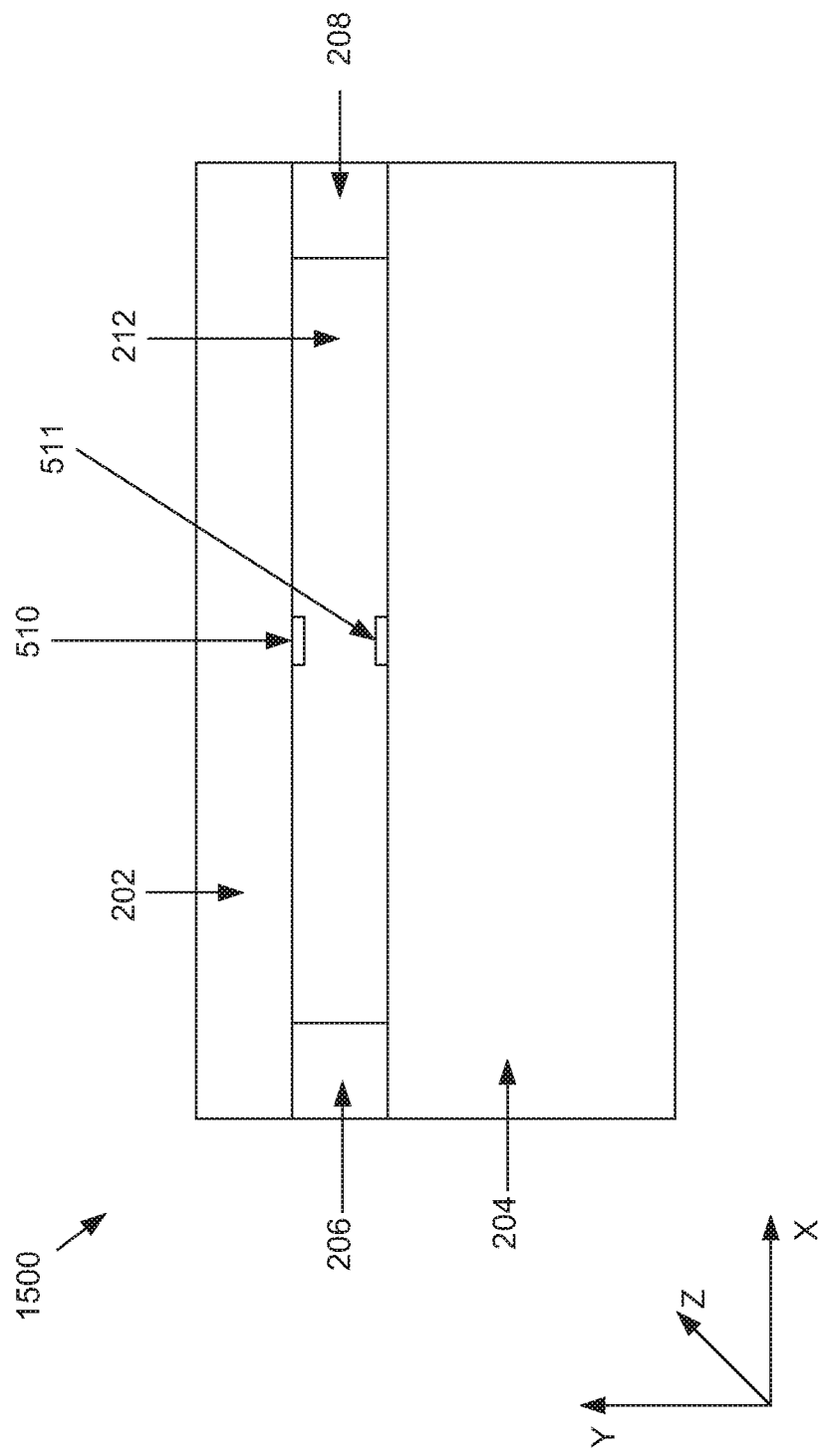
FIG. 15 illustrates an example capacitive micromachined ultrasound transducer with a high contact resistance bump on a top electrode and on a bottom electrode, in accordance with various embodiments.

FIG. 15 illustrates an example capacitive micromachined ultrasound transducer 1500 with the high contact resistance bump 510 on the top electrode 202 and the high contact resistance bump 511 on the bottom electrode 204. It may be noted that one or both of the top electrode and the bottom electrode may comprise one or more high contact resistance bumps. Where there is not a matching second bump on the top and bottom electrode for the first bump on the bottom or top electrode, the first bump may be thicker than the bump that does have a matching bump. The sidewalls 206/208 may define the effective gap ($g_{eff}$) comprising the bumps 510, 511 and the gap 212.

Figure 16:
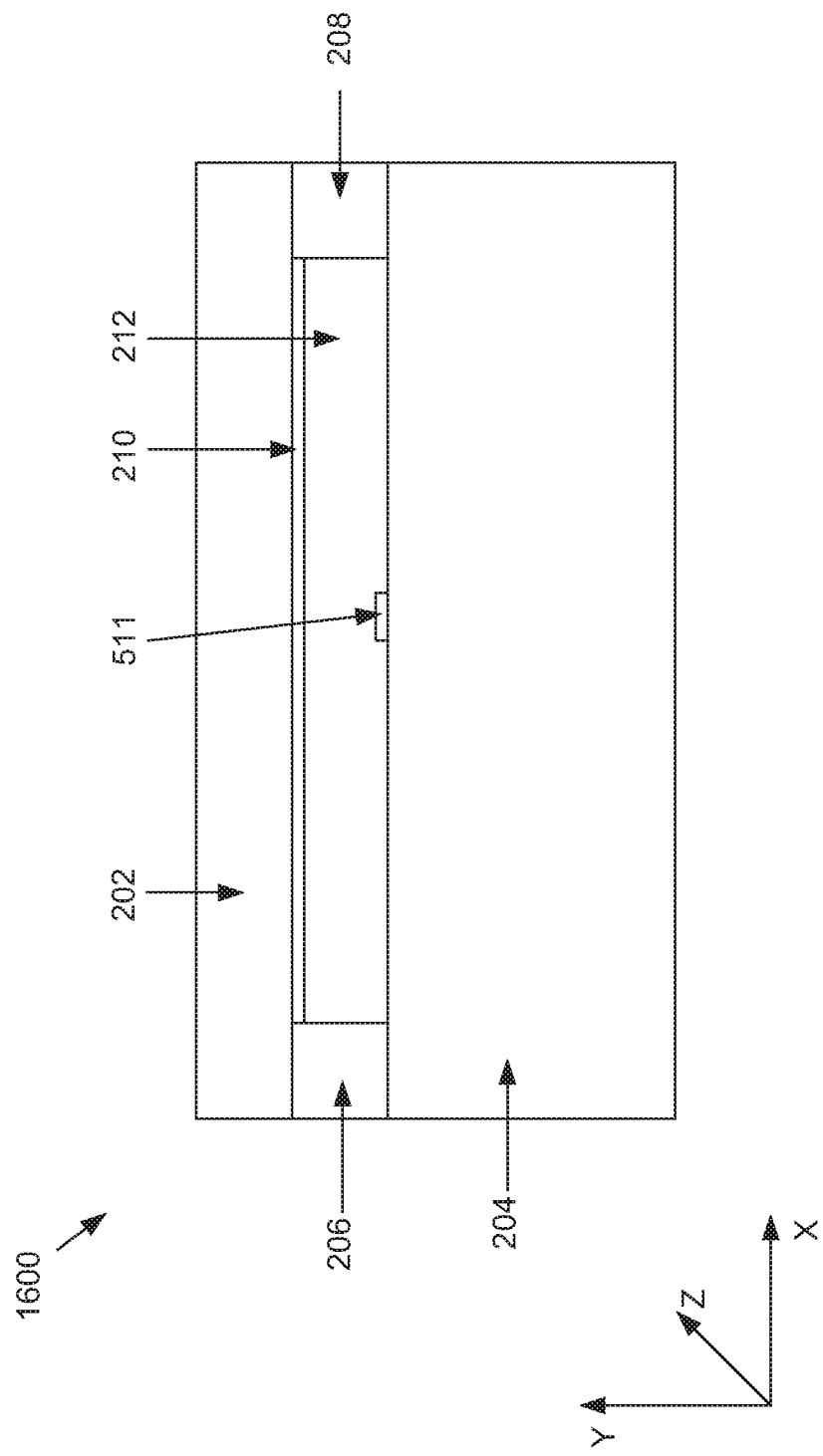
FIG. 16 illustrates an example capacitive micromachined ultrasound transducer with a high contact resistance bump on a bottom electrode and a high contact resistance layer on a top electrode, in accordance with various embodiments.
Figure 17:
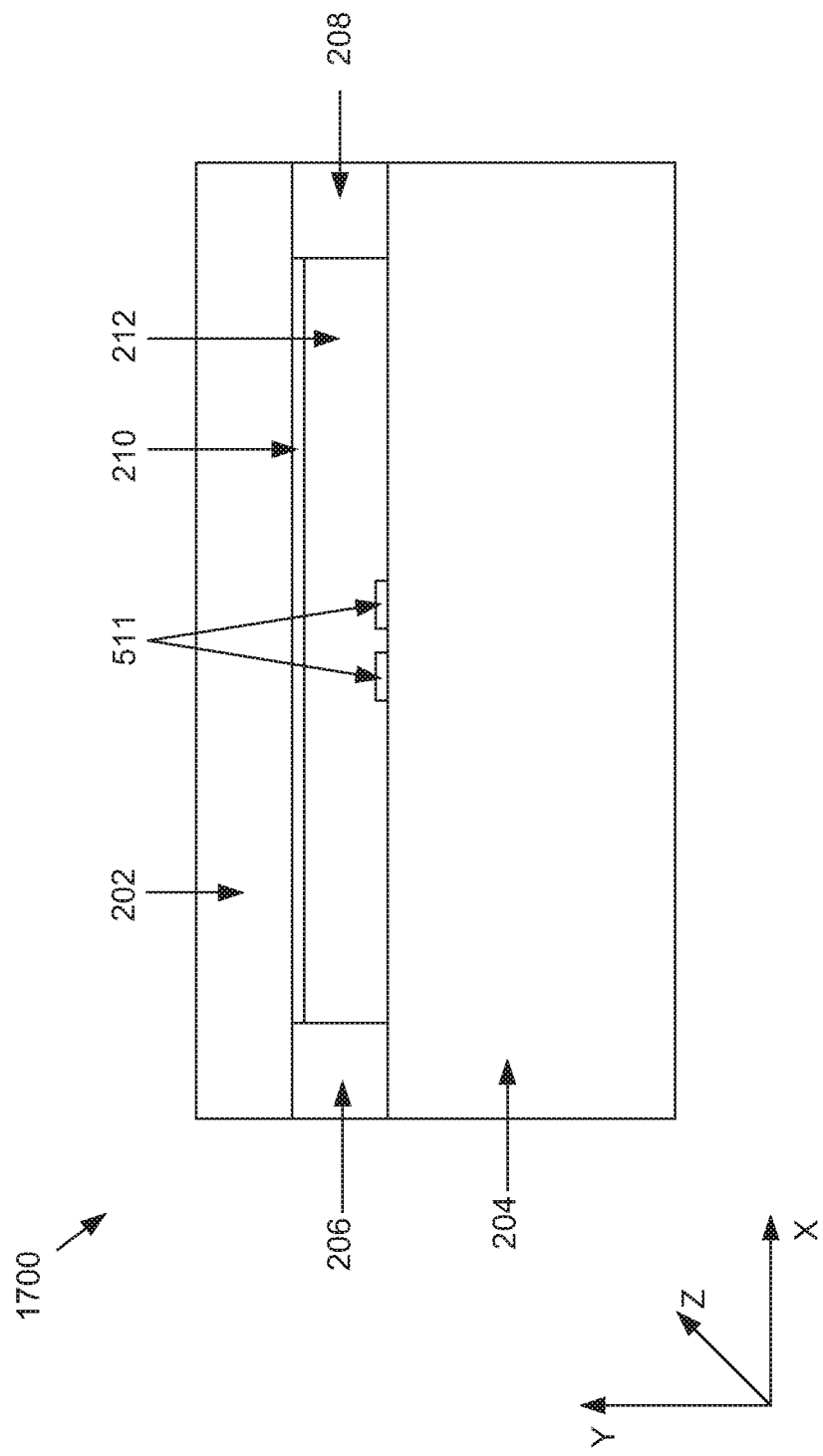
FIG. 17 illustrates an example capacitive micromachined ultrasound transducer with multiple high contact resistance bumps on a bottom electrode and a high contact resistance layer on a top electrode, in accordance with various embodiments.

FIGS. 16-17 are similar to FIGS. 8 and 12 except that there are one or more high contact resistance bumps 511 on the bottom electrode 204 and the high contact resistance layer 210 on the top electrode 202. Accordingly, the sidewalls 206/208 may define the effective gap ($g_{eff}$) comprising the bump 511, the high contact resistance layer 210, and the gap 212.

FIG. 18 illustrates a cross-section view along Z axis of an example capacitive micromachined ultrasound transducer with a high contact resistance bump on a top electrode, in accordance with various embodiments. Referring to FIG. 18, there is shown a cross-section view in Y-Z plane of the CMUT shown in FIG. 5. The single bump 510 visible in FIG. 5 in the X-Y plane may be, for example, a plurality of high contact resistance bumps 510 when seen in the Y-Z plane of FIG. 18. While three bumps 510 are shown in FIG. 18, in various embodiments there may be one bump, two bumps, or more than three bumps. The plurality of bumps 510 shown in FIG. 18 may be, for example, substantially centered along a depth of the CMUT 500 (e.g., along the direction Z). Additionally, an embodiment may have a single bump 510 that spans a length of the depth in the Z direction of the CMUT 500.

A CMUT as disclosed may have any geometric shape when viewed from the top (for example, the X-Z plane). As examples, a CMUT may be circular, elliptical, oval, one of the many polygonal shapes, etc. Additionally, while a single bump or multiple bumps may be substantially centered along a direction of a CMUT, various embodiments of the disclosure may place a bump or bumps in various positions along a direction of the CMUT.

Additionally, while various figures disclosed a surface having either a high contact resistance layer or a high contact resistance bump(s), various embodiments of the disclosure may comprise a combination of high contact resistance layer(s) and high contact resistance bump(s).

Additionally, the top electrode 202 of a capacitive transducer may be perforated, and this may be referred to as a perforated plate. It may be noted that when the top electrode is perforated, the top layer 210 may have corresponding perforations or is placed around the perforations so as to not obstruct the perforations. Similarly, when there are one or more bumps 510/610/710 on the top electrode 202, the bump(s) 510/610/710 may be placed to not obstruct the perforations.

While various embodiments were disclosed with respect to capacitive micromachined ultrasound transducers, the disclosure may apply to other types of transducers other than ultrasound transducers. For example, any type of a MEMS device that uses insulation layers may use the disclosed embodiments to solve the problem of charging in one or more insulated layers. Also, while transducers were described in places as being used for medical imaging, various other types of imaging may also make use of the transducers. For example, imaging devices may be used for ultrasound/acoustic sensing, non-destructive evaluation (NDE), ultrasound therapy (High Intensity Focused Ultrasound (HIFU), etc.), etc., in addition to ultrasound imaging of humans, animals, etc.

Accordingly, as can be seen, the disclosure provides for a capacitive transducer comprising a top electrode and a bottom electrode, a sidewall between the top electrode and the bottom electrode, where the sidewall is configured to separate the top electrode and the bottom electrode by a gap, and a high contact resistance part on one or both of a bottom side of the top electrode or a top side of the bottom electrode.

The high contact resistance part may comprise one or both of: a high contact resistance layer that spans substantially a width of the bottom side of the top electrode, or a high contact resistance layer that spans substantially a width of the top side of the bottom electrode. The high contact resistance part may comprise a high contact resistance layer that spans one or both of: at least a portion of a width of the bottom side of the top electrode, or at least a portion of a width of the top side of the bottom electrode.

The high contact resistance part may comprise one or more high contact resistance bumps along one or both of the bottom side of the top electrode or the top side of the bottom electrode. The one or more high contact resistance bumps may be, for example, substantially centered along the width of the capacitive transducer, such as along one of the axis of the capacitive transducer. A shape of a cross-section of the one or more high contact resistance bumps may be one of: rectangular, triangular, or rounded.

The one or more high contact resistance bumps may comprise a first high contact resistance bump on the top electrode and a second high contact resistance bump on the bottom electrode that corresponds to the first high contact resistance bump.

The high contact resistance part may comprise one of: one or more high contact resistance bumps on a bottom side of the top electrode and a high contact resistance layer that spans at least a portion of a width of the top side of the bottom electrode, or one or more high contact resistance bumps on a top side of the bottom electrode and a high contact resistance layer that spans at least a portion of a width of the bottom side of the top electrode.

The high contact resistance part may comprise material from at least III-V section or the II-VI section of the periodic table. The high contact resistance part may comprise, for example, gallium arsenide, cadmium zinc telluride, etc. An electrical contact resistivity of the high contact resistance part may be greater than, for example, $10^7$ $\Omega*cm^2$.

The gap may be filled with gas such as, for example, air. The capacitive transducer may comprise, for example, a perforated plate. The perforated plate may be, for example, the top electrode 202. It may be noted that when the top electrode is perforated, the top layer 210 may have similar corresponding perforations or the top layer 210 is placed around the perforations so as to not obstruct the perforations. Similarly, when there are one or more bumps 510/610/710 on the top electrode 202, the bump(s) 510/610/710 may be placed to not obstruct the perforations.

The capacitive transducer may be configures such that the gap may be air-tight, where the gap may comprise, for example, a substantially gas-free or air-free vacuum.

The disclosure may also provide for a capacitive micromachined ultrasound transducer (CMUT), comprising a top electrode and a bottom electrode, a sidewall between the top electrode and the bottom electrode. The sidewall may be configured to separate the top electrode and the bottom electrode by a gap, where the gap comprises a substantially gas-free vacuum. The CMUT may also comprise a high contact resistance part on one or both of a bottom side of the top electrode or a top side of the bottom electrode, where the high contact resistance layer may comprise one of gallium arsenide or cadmium zinc telluride. The high contact resistance part may comprise one of a high contact resistance layer or a high contact resistance bump.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What are claimed:

1. A capacitive transducer, comprising:
   a top electrode and a bottom electrode;
   a sidewall between the top electrode and the bottom electrode, wherein the sidewall is configured to separate the top electrode and the bottom electrode by a gap, wherein each of the top electrode and the bottom electrode extend at least an entire width of the gap; and
   a high contact resistance part on one or both of a bottom side of the top electrode or a top side of the bottom electrode,
   wherein an effective gap within the sidewall and between the top electrode and the bottom electrode consists of the gap and the high contact resistant part, and
   wherein the high contact resistant part comprises at least material from III-V section of the periodic table or II-VI section of the periodic table.

2. The capacitive transducer of claim 1, wherein the high contact resistance part comprises one or both of:
   a high contact resistance layer that spans a width of the bottom side of the top electrode within the effective gap; and
   a high contact resistance layer that spans a width of the top side of the bottom electrode within the effective gap.

3. The capacitive transducer of claim 1, wherein the high contact resistance part comprises a high contact resistance layer that spans one or both of:
   a majority of a width of the bottom side of the top electrode; and
   a majority of a width of the top side of the bottom electrode.

4. The capacitive transducer of claim 1, wherein the high contact resistance part comprises one or more high contact resistance bumps along one or both of the bottom side of the top electrode or the top side of the bottom electrode.

5. The capacitive transducer of claim 4, wherein the one or more high contact resistance bumps are substantially centered along a width of the capacitive transducer.

6. The capacitive transducer of claim 4, wherein a shape of a cross-section of the one or more high contact resistance bumps is one of: rectangular, triangular, or rounded.

7. The capacitive transducer of claim 4, wherein the one or more high contact resistance bumps comprise a first high contact resistance bump on the top electrode and a second high contact resistance bump on the bottom electrode that is aligned with the first high contact resistance bump.

8. The capacitive transducer of claim 1, wherein the high contact resistance part comprises one of:
   one or more high contact resistance bumps on a bottom side of the top electrode and a high contact resistance layer that spans a width of the top side of the bottom electrode within the effective gap; or
   one or more high contact resistance bumps on a top side of the bottom electrode and a high contact resistance layer that spans a width of the bottom side of the top electrode within the effective gap.

9. The capacitive transducer of claim 1, wherein the high contact resistance part comprises gallium arsenide.

10. The capacitive transducer of claim 1, wherein the high contact resistance part comprises cadmium zinc telluride.

11. The capacitive transducer of claim 1, wherein an electrical contact resistivity of the high contact resistance part is greater than $10^7$ $\Omega*cm^2$.

12. The capacitive transducer of claim 1, wherein the gap is a gas-filled gap.

13. The capacitive transducer of claim 1, wherein the gap is an air-filled gap.

14. The capacitive transducer of claim 1, wherein the gap is an air-tight gap.

15. The capacitive transducer of claim 14, wherein the gap is a substantially gas-free vacuum.

16. The capacitive transducer of claim 1, comprising a perforated plate.

17. A capacitive micromachined transducer, comprising:
    a top electrode and a bottom electrode;
    a sidewall between the top electrode and the bottom electrode, wherein the sidewall is configured to separate the top electrode and the bottom electrode by a gap, wherein each of the top electrode and the bottom electrode extend at least an entire width of the gap, and wherein the gap comprises a substantially gas-free vacuum; and
    a high contact resistance part on one or both of a bottom side of the top electrode or a top side of the bottom electrode,
    wherein the high contact resistance part comprises one of gallium arsenide or cadmium zinc telluride, and
    wherein an effective gap within the sidewall and between the top electrode and the bottom electrode consists of the gap and the high contact resistance part.

18. The capacitive micromachined transducer of claim 17, wherein the high contact resistance part comprises one of a high contact resistance layer or a high contact resistance bump.

* * * * *